US006258349B1

(12) United States Patent
de Vecchi

(10) Patent No.: US 6,258,349 B1
(45) Date of Patent: Jul. 10, 2001

(54) DEODORANT COMPOSITION ESPECIALLY FORMULATED FOR MOTORCARS AND ENVIRONMENTS, WITH HIGH CHARACTERISTICS OF STABILITY AND RELEVENT PRODUCTION PROCESS

(75) Inventor: Monna de Vecchi, Porza (CH)

(73) Assignee: Beta Pictoris Inc., Milan (IT)

( * ) Notice: Subject to any disclaimer, the term of this patent is extended or adjusted under 35 U.S.C. 154(b) by 0 days.

(21) Appl. No.: 09/441,772

(22) Filed: Nov. 17, 1999

(30) Foreign Application Priority Data

Mar. 23, 1999 (IT) .............................................. MI99A0586

(51) Int. Cl.$^7$ ....................................... A61L 9/013

(52) U.S. Cl. ........................ 424/76.3; 424/76.1; 424/76.2

(58) Field of Search .................................... 424/76.1–76.4

(56) References Cited

U.S. PATENT DOCUMENTS 5,665,292 * 9/1997 Tanaka et al. ......................... 264/86

* cited by examiner

*Primary Examiner*—Jose' G. Dees
*Assistant Examiner*—Konata M. George
(74) *Attorney, Agent, or Firm*—Notaro & Michalos P.C.

(57) ABSTRACT

It is hereinafter described a deodorant composition for domestic environments consisting of a mixture of perfume and solubilizing agent incorporated in a support whose main components include a carragenine mixture blended to setting gypsum.

The composition in particular includes the following components:

carragenine mixture: 1–4% (weight)
ethoxylated hydrogenated 40EO castor oil: 4–10% (weight)
isothiazolinonic preservative: 0.01–0.08% (weight)
setting gypsum: 20–30% (weight)
perfume: 5–20% (weight)
water: q.s. to 100% (weight).

3 Claims, No Drawings

DEODORANT COMPOSITION ESPECIALLY FORMULATED FOR MOTORCARS AND ENVIRONMENTS, WITH HIGH CHARACTERISTICS OF STABILITY AND RELEVENT PRODUCTION PROCESS

FIELD AND BACKGROUND OF THE INVENTION

This invention relates to a deodorant composition for environments, designed to be used in domestic environments or cars, with improved characteristics of stability. in particular with characteristics suited to avoid synaeresis (i.e. leakage of fluids at high temperatures).

This invention especially refers to a deodorizer whose main components consist of a carragenine mixture blended to setting gypsum.

The composition is finally completed with ethoxylated hydrogenated castor oil, perfume with suitable preservative substances.

A composition is therefore obtained, having improved characteristics of mechanical resistance with long-lasting and steady diffusion of the perfume, thanks to the particular choice of the support, consisting of a material having a really limited shrinkage with time and minimum variation in dimensions due to the temperature.

The invention also concerns the manufacturing process for the production of the above mentioned compound. Different kinds of deodorizers for domestic environments are known, consisting of a perfuming substance dispersed in a support which allows its gradual diffusion.

These deodorizers are sold in packing such as cases or similar having a series of perforations which limit the diffusion of perfume, or in housings provided with an adjustable cover opening which allows to vary the intensity of the perfume diffused and the life of the substance itself.

In certain cases these compositions consist of a paste with volatile substances in which the perfumed essence to be diffused in the environment is incorporated.

In other cases is used a porous support imbued with perfumed essence which shall also be gradually diffused.

Most of these known compositions result to have a minimum stability and likewise present a rather quick deterioration so that, after a few days, the diffusion of the perfume of the composition is practically imperceptible.

In other cases the compositions are sensitive to heat and may rapidly deteriorate at a temperature of about 35–40° C.

SUMMARY OF THE INVENTION

This invention relates to this sector; it proposes a deodorant composition with high characteristics of stability, enough to keep itself unchanged for a long time and to be practically insensitive to variations in temperature.

These characteristics are obtained by a composition including, as main components, a carragenine mixture, blended to setting gypsum.

This composition gives to the product a considerable mechanical resistance and makes it especially suited to be used as car deodorizer and allows to incorporate a large quantity of perfume, ensuring a constant and lasting diffusion.

For a better understanding of this invention, a preferred example of composition according to the invention will follow.

DESCRIPTION OF THE PREFERRED EMBODIMENTS

The deodorant composition results as follows:
carragenine mixture: 1–4% (weight)
a ethoxylated hydrogenated 40EO 4 castor oil: 4–10% (weight)
a isothiazolinonic preservative: 0.01–0.08% (weight)
a setting gypsum: 20–40% (weight)
perfume: 5–20% (weight)
water: q.s. to 100% (weight)

The carragenine mixture can be constituted e.g. by the compound marketed by Shemberg Co. with Puregell AFG 9503 trademark: the hydrogenated castor oil can be chosen among the products marketed by the trademarks Cremophor RH 40 and Cremophor (BASF) Sabopal ELH 40 (SABO); Sabowax BLII 40 (SABO), while the preservative can be e.g. constituted by Kathon OG (ROHM & HAAS). Preferably the composition shall have the following formula:

Puregell AFG9503: 2% (weight)
Etoxilated hydrogenated 40EO castor oil: 5% (weight)
Kathon CG: 0.05% (weight)
Setting gypsum: 30% (weight)
Perfume: 10%(weight)
Water: q.s. to 100% (weight)

As stated above, the presence of the carragenine mixture blended to the setting gypsum gives to the composition:

high mechanical resistance, particularly useful for the production of a deodorizer to be used inside a car, which must therefore be shakeproof and must not move inside the housing during the motion of the car;

a constant and lasting diffusion of the perfume, since the particular mixture of support for the perfume has a minimum shrinkage with time and variation in dimensions due to the temperature, keeping this way a "reserve" effect of the perfume contained therein;

possibility of inclusion of a large quantity of perfume (10% and more), chance impossible for the other deodorants.

The preparation of the composition may be made according the following:

Manufacturing Process after removing from the system all the possible remains of other perfumes which may interfere with the perfume of the product and after checking that the water coming from the water system is odourless, without chlorine or other oxidizers which may alter the perfume, it is then possible starting the production.

Fill a mixer with system water at room temperature and slowly add Puregall AFG 9503, shaking constantly. Keep on shaking, at room temperature, until complete dispersion of the gelling agent.

After verifying the absence of lumps, it is possible starting the heating operation.

The mixture temperature is rised, under shaking, to a temperature between 80° C. and 90° C. and the mixture is kept at this temperature for a lapse of time from 20 to 30 minutes.

Then add Kathon CG and carefully mix.

Blend setting gypsum under vigorous shaking, avoiding the forming of lumps and constantly keeping the temperature at 80–90° C.

In an separate mixer, mix the etoxilated hydrogenated 40EO castor oil with the perfume and then pour the mixture of perfume and solubilizing agent in the main mixer under shaking, mixing until homogenous distribution of the perfume in the mass.

After the completion of the mixing operation, the product can be placed in the molds as rapidly as possible in order to avoid losses or degradations of the perfume.

This process allows to get a solid product, having good mechanical resistance, able to gradually diffuse the perfume and with a constant flow.

The mechanical characteristics of the product allow the use both as deodorizer for domestic environments and deodoriser for cars.

A skilled in the art may make several changes and different versions which must be considered included within the competence of this invention.

What is claimed is:

1. Deodorant composition for domestic environments including a mixture of perfume and solubilizing agent incorporated into a support where the support includes as main components a mixture of carragenine blended to setting gypsum, the composition comprising:

a carragenine mixture in an amount of 1–4% by weight;

an ethoxylated hydrogenated 40EO castor oil in an amount of 4–10% by weight;

an isothiazolinonic preservative in an amount of 0.01–0.08% by weight;

a setting gypsum in an amount of 20–30% by weight;

a perfume in an amount of 5–20% by weight; and water to reach 100% by weight.

2. Deodorant composition according to claim 1, comprising the following components:

carragenine mixture: 2% (weight)

ethoxylated hydrogenated 40EO castor oil: 5% (weight)

isothiazolinonic preservative: 0.05% (weight)

setting gypsum: 30% (weight)

perfume: 10% (weight)

water: q.s. to 100% (weight).

3. Manufacturing process for the production of a deodorant composition according to claim 1, comprising following the steps:

addition of a mixture of carragenine to water under shaking;

heating of the mixture until a temperature of 80–90° C.;

addition of a preservative;

addition of setting gypsum under shaking;

separate preparation of a mixture of ethoxylated hydrogenated 40EO castor oil with perfume;

addition of the above mentioned mixture of castor oil and perfume to the main mixture under shaking;

straining of the mixture obtained through this process into the molds and hardening.

* * * * *